(12) United States Patent
Namin et al.

(10) Patent No.: US 11,452,744 B2
(45) Date of Patent: Sep. 27, 2022

(54) LIQUID AMNION TRANSPLANT PRODUCT

(71) Applicant: Vivex Biologies Group, Inc., Atlanta, GA (US)

(72) Inventors: Shabnam Namin, Miami, FL (US); Gaëtan Jean-Robert Delcroix, Miami, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 238 days.

(21) Appl. No.: 17/071,570

(22) Filed: Oct. 15, 2020

(65) Prior Publication Data

US 2021/0023144 A1    Jan. 28, 2021

Related U.S. Application Data

(60) Continuation of application No. 16/503,747, filed on Jul. 5, 2019, now Pat. No. 10,842,825, which is a division of application No. 14/823,770, filed on Aug. 11, 2015, now Pat. No. 10,413,572.

(51) Int. Cl.
*A61K 35/50* (2015.01)

(52) U.S. Cl.
CPC .................... *A61K 35/50* (2013.01)

(58) Field of Classification Search
CPC ............ A61K 35/50; A61B 10/0048; A61B 10/0233; A61B 8/0841; A61B 10/0283; A61L 2/081; A61L 2/087; A61M 1/0011; A61M 2202/0437; A61M 2202/0494
See application file for complete search history.

(56) References Cited

U.S. PATENT DOCUMENTS

2015/0025366 A1    1/2015   Harrell

OTHER PUBLICATIONS

Larrabee PB et al, "Presence of Filterable and Nonfilterable Cell-Free mRNA in Amniotic Fluid" Clinical Chemistry, May 2005, 51(6), pp. 1024-1026, DOI: 10.1373/clinchem.2004.047670 (Year: 2005).

*Primary Examiner* — Aaron J Kosar
(74) *Attorney, Agent, or Firm* — David L. King

(57) ABSTRACT

A transplant product made from human amniotic fluid has a supernatant from filtered and centrifuged amniotic fluid, the amniotic fluid when recovered aseptically having a clear, translucent to slightly pink or tan color. The supernatant had been taken from the amniotic fluid which had been passed through a 170 to 260 micron blood filter, then centrifuged for 5 minutes or more at 400 g and thereafter the supernatant was separated from a pellet of debris, leaving the biochemical properties intact, wherein the supernatant is cryofrozen in sized cryovials having 0.25 to 2.0 ml of the supernatant at a temperature of −65 degrees or less prior to use and the transplant products method of use. The transplant product contains cellular material, cell fragments, proteins and growth factors maintaining the biochemical properties and is non-immunogenic while having particles up to 170 microns being passable through a 30 gauge syringe for injection.

3 Claims, 7 Drawing Sheets

LIQUID AMNION TRANSPLANT PRODUCT

RELATED APPLICATIONS

This application is a continuation of co-pending U.S. application Ser. No. 16/503,747 filed on Jul. 5, 2019 entitled, "Liquid Amnion Transplant Product"; which is a division of U.S. application Ser. No. 14/823,770 now U.S. Pat. No. 10,413,572 issued on Sep. 17, 2019.

TECHNICAL FIELD

This invention relates to the manufacturing of a transplant product derived from human amniotic fluid (AF). The transplant product is categorized as a liquid version of amniotic tissue.

BACKGROUND OF THE INVENTION

Within the uterus of a pregnant woman, a growing fetus is surrounded and cushioned by amniotic fluid, a watery liquid within the amnion Amniotic fluid is one of the main samples used for the medical examination of the pregnant woman and her fetus.

Traditionally, during a Caesarean section, after cutting through the uterus, the amniotic fluid will be suctioned away and discarded to make more room Amniotic fluid contains cells, electrolytes, growth factors, carbohydrates, lipids, proteins, amino acids, lactate, pyruvate, enzymes and hormones Amniotic fluid is also a source of stem cells which ideally should be isolated and separately cultivated for cell therapy purposes. While amniotic fluid cells can be obtained from a small amount of fluid during amniocentesis, these amounts are insufficient for a larger scale harvesting of biomolecules or culturing of the stem cells comprising amniotic fluid.

In US 2015/0025366 entitled "Method for Obtaining Sterile Human Amniotic Fluid and Uses Thereof" published Jan. 22, 2015 stated, there is a recognized need in the art for an improved means for obtaining sterile amniotic fluid for use in research and the development of therapeutic products. Particularly, the prior art is deficient in methods for obtaining sterile human amniotic fluid with minimal or no risk to a pregnant woman or fetus by collecting the amniotic fluid prior to an elective Caesarean section. Also the prior art is deficient in methods for obtaining sterile human amniotic fluid devoid of cells which may create unwanted reactions due to their allogenic characters on the patients to be treated. The inventor, Harrell, claimed to fulfill this longstanding need and desire in the art to improve the safety of amniotic fluid in its medical uses and taught how to sterile filter the fluid.

The prior art method of obtaining sterile filtered human amniotic fluid from an individual. This method comprises the steps of obtaining sterile human amniotic fluid from an individual, removing cells, large particles and other undissolvables from said human amniotic fluid by high speed centrifugation, followed by membrane filtration. The first step is to centrifuge the amniotic fluid in swing out buckets adapted to swing out rotors or other centrifugation bottles in angle rotors at about 5,000 rpm to about 10,000 rpm for about 30 minutes to about 60 minutes. The supernatant is then filtered using filters with a pore size of about 5 µm to about 10 µm to obtain the first filtrate, then filtering said first filtrate through filters with a pore size of about 1.0 µm to obtain a second filtrate, filtering the second filtrate through filters with the pore size of 0.45 µm or/and 0.2 µm to obtain a sterilely filtered amniotic fluid. In case of a final membrane filtration limited to 0.45 µm, it is preferable to repeat a second filtration on a second 0.45 µm membrane, to increase the sterility assurance level. The sterile amniotic fluid retains the growth factors from the raw amniotic fluid. In this method, the first centrifugation step may be replaced by depth filtration through available filtration systems, however this option is not preferred because it leads to important volume losses and undesirable adsorption of growth factors by the filtration media.

This technique disclosed by Harrell achieved a sterile fluid that removed all particles down to 0.2 micron. All cells and particulate greater than the 0.2 micron are removed, leaving a fluid devoid of much of the beneficial biochemical particles needed to be useful in medical treatments.

The present invention discloses a method to recover amniotic fluid and maintain particles in sizes up to 170 microns to 260 microns, over 100 times greater, but maintaining a non-immunogenic product having superior biochemical properties suitable for direct injection into patients.

SUMMARY OF THE INVENTION

A method for a transplant product made from human amniotic fluid has the steps of aseptically recovering a volume of greater than 100 ml of human amniotic fluid from a woman, visualizing the fluid to confirm the removed volume has a pink to clear color and contains no vernix prior to filtering and then filtering said amniotic fluid through a blood filter with a pore size of 170 to 260 microns. The process of filtering the amniotic fluid is performed to ensure the biochemical properties of the tissue remain intact. Placing the filtered amniotic fluid in a plurality of centrifuge tubes by the step of transferring the filtered amniotic fluid tissues in the centrifuge tubes into a calibrated centrifuge; centrifuging at a centrifuge cycle of 5 minutes at 400 g. When the cycle is complete, the centrifuged fluid is separated into a supernatant from the amniotic fluid and a pellet containing debris; the supernatant is carefully removed and separated from the pellet and set aside for further processing.

Thereafter, aliquoting the supernatant of liquid amnion into sized cryovials of transplant product sizes in the range of 0.25 ml to 2.0 ml. A smaller volume of the 0.25 mL and 0.5 mL transplant product size is placed into 1.8 mL cryovials and a larger volume 1.0 mL and 2.0 mL transplant product size is placed into the larger 4.5 mL cryovials. The volumes are aliquoted into the appropriate sized cryovials using a calibrated pipette. Randomly selected filled cryovials are used for liquid microbiology cultures that represent the transplant product. The cryovials after being filled with supernatant from the amniotic fluid are packaged, inspected and stored in the absence of a cryopreservative in a −65° C. or colder freezer. The sized volume of frozen supernatant when thawed and resuspended in a diluent, such as sterile water, for use has a viscosity approximating water and is injectable through a 30 gauge needle. The supernatant of amniotic fluid when thawed is non-immunogenic and has preserved the biochemical propertied.

A method of treatment using the transplant product involves the steps of taking a sterile syringe with at least a 30 gauge needle and filling it with the thawed and resuspended supernatant of amniotic fluid and injecting the fluid into the patient to be treated. The patient to be treated has one or more of the following conditions of damaged or injured tissue, or a degenerative tissue condition and the injection of the supernatant from amniotic fluid is a treatment for said condition.

A transplant product made from human amniotic fluid has a supernatant from filtered and centrifuged amniotic fluid, the amniotic fluid when recovered aseptically having a clear, translucent to slightly pink or tan color. The supernatant had been taken from the amniotic fluid which had been passed through a 170 to 260 micron blood filter, then centrifuged for 5 minutes or more at 400 g and thereafter the supernatant was separated from a pellet of debris, leaving the biochemical properties intact, wherein the supernatant is cryofrozen in sized cryovials having 0.25 to 2.0 ml of the supernatant at a temperature of −65 degrees or less prior to use. The transplant product contains cell or cell fragments, proteins and growth factors maintaining the biochemical properties and is non-immunogenic while having particles up to 170 microns being passable through a 30 gauge syringe for injection.

Definitions

Vernix caseosa, also known as vernix, is the waxy or cheese-like white substance found coating the skin of newborn human babies. Vernix starts developing on the baby in the womb around 18 weeks into pregnancy.

BRIEF DESCRIPTION OF THE DRAWINGS

The invention will be described by way of example and with reference to the accompanying drawings in which.

DETAILED DESCRIPTION OF THE INVENTION

Figure 1:
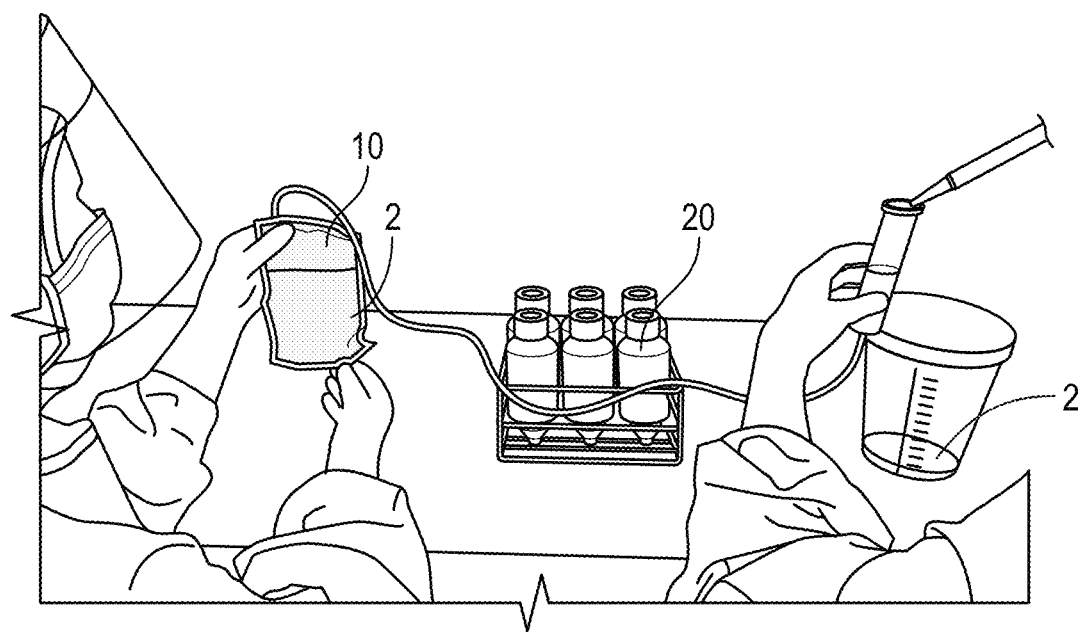
FIG. 1 is a photograph of amniotic fluid that is being aseptically transferred to a blood bag.
Figure 2:
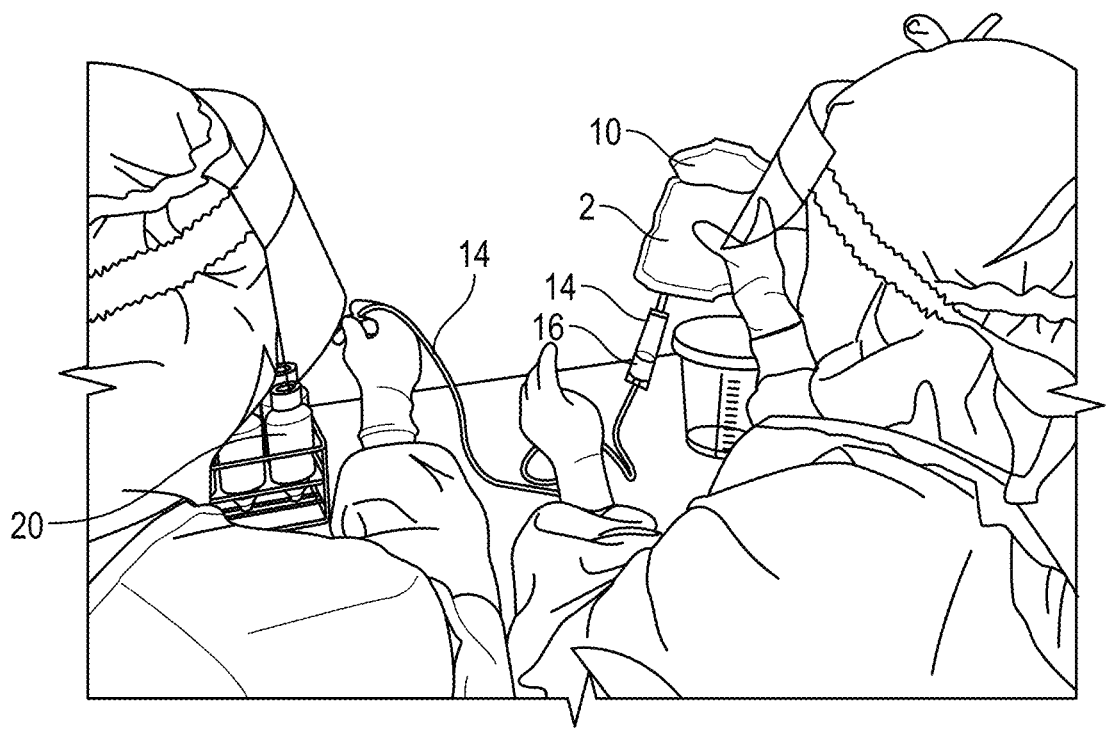
FIG. 2 is a photograph showing the amniotic fluid in the blood bag being filtered into centrifuge tubes.
Figure 3:
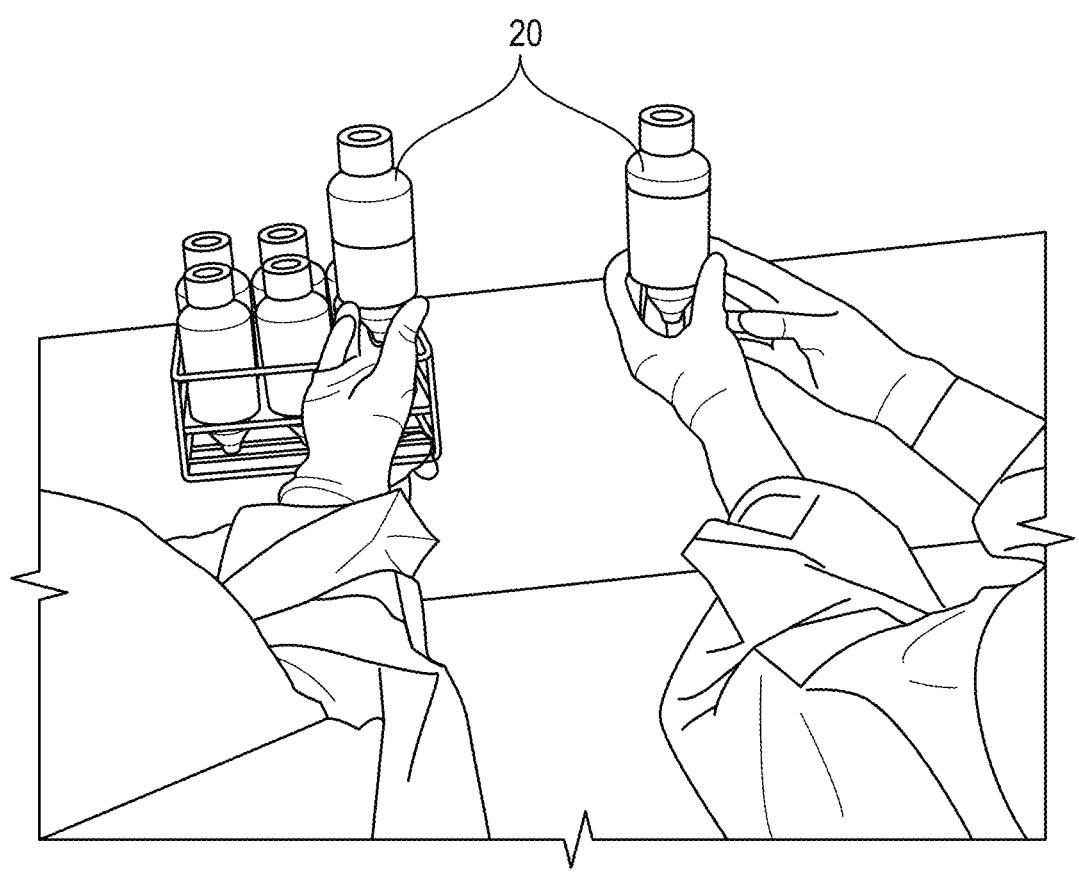
FIG. 3 is a photograph showing centrifuge tubes after being filled with the filtered amniotic fluid before being centrifuged.

With reference to photographs 1-3, technicians are shown with a blood bag 10 filled with a volume of amniotic fluid 2 which will be processed through a blood filter 16 and collected into small containers 20. As shown in FIG. 1, the technician is pipetting a volume of the amniotic fluid 2 into a syringe connected by tubing which is thereby filling the blood bag 10. The blood bag 10 is then connected to an IV tube or set 14 with a blood filter 16 at the bottom of the drip chamber and then the fluid 2 is delivered to a centrifuge container 20, as shown in FIG. 2. As shown in FIG. 3, each technician is holding a container of the amniotic fluid. As shown in the photographs, the amniotic fluid 2 recovered from a pregnant woman who had elected cesarean is shown with a slightly reddish color, this color in the photograph is unacceptable. In practice, the amniotic fluid 2 should be clear, translucent, slightly pink or slightly tan. The deep red color as shown is exemplary of an unacceptable volume of amniotic fluid 2 because it has too much blood product and debris. Properly collected amniotic fluid 2 will be substantially clearer than that as illustrated in FIGS. 1-3. For the purposes of this invention, when the amniotic fluid 2 is recovered properly in an aseptic technique, and used during the filtering step explained in diagram 7 prior to centrifuging, the material will have the color as indicated which should be confirmed to be clear, translucent, slightly pink or slightly tan.

Figure 4:
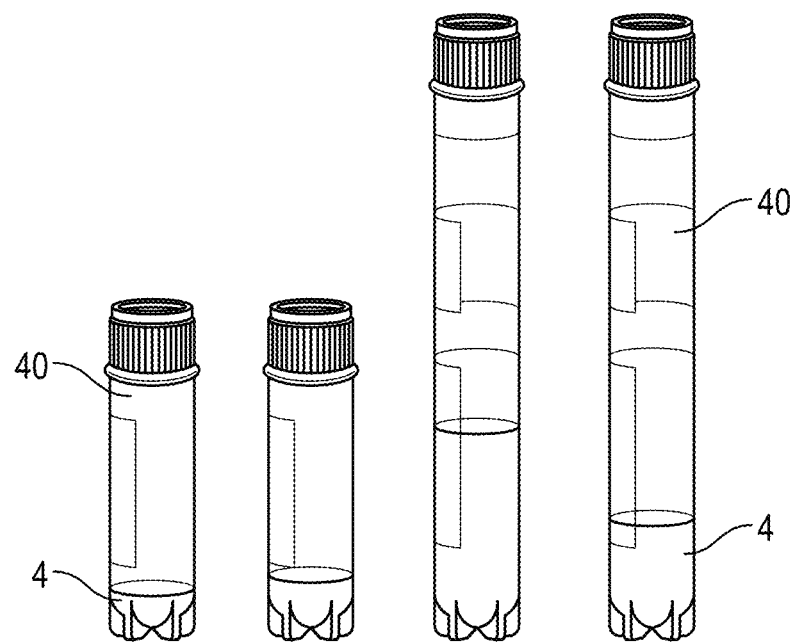
FIG. 4 is a photograph showing the liquid supernatant from the amniotic fluid after the centrifuge process.
Figure 5:
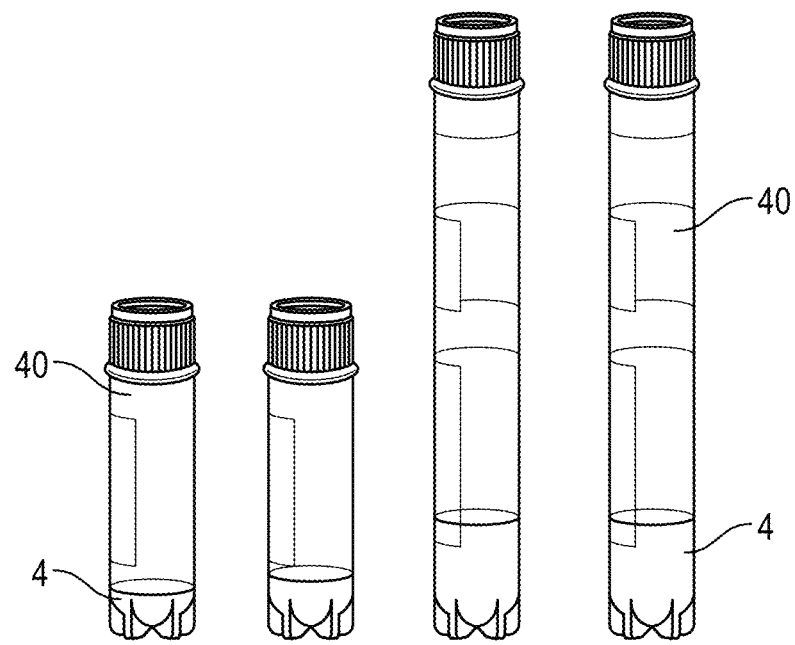
FIG. 5 is a photograph showing frozen supernatant from the amniotic fluid after the centrifuge process.
Figure 6:
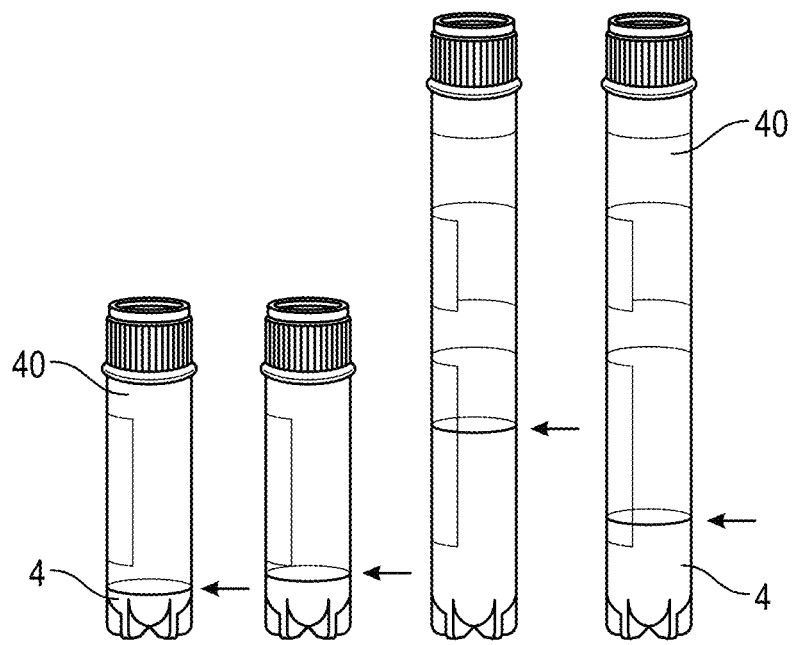
FIG. 6 is a photograph showing a clear supernatant from the amniotic fluid after the centrifuge process.
Figure 7:
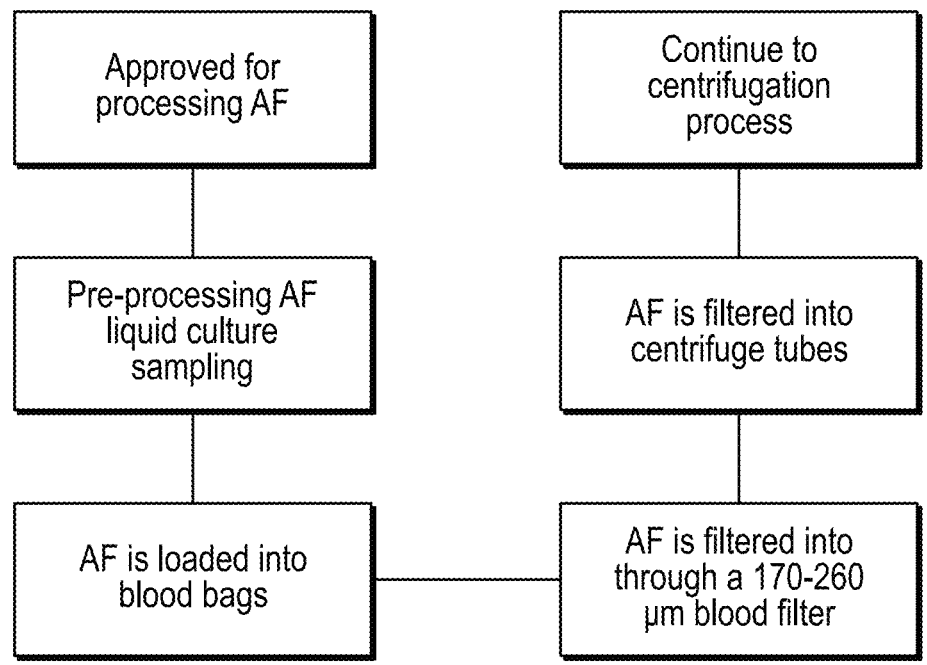
FIG. 7 is a flow chart detailing the filtering process of the amniotic fluid.
Figure 8:
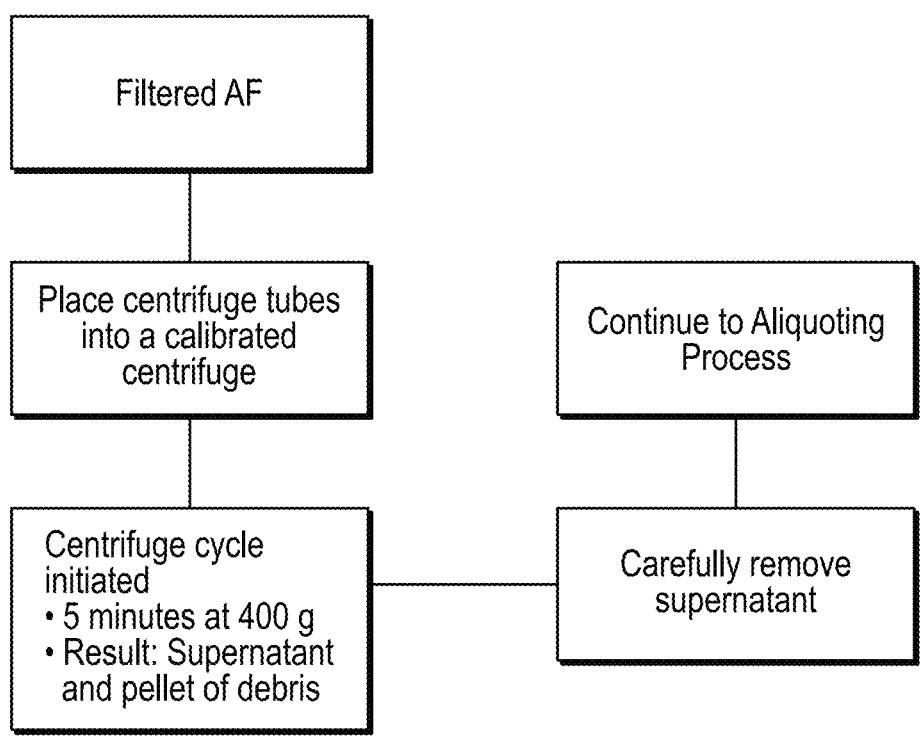
FIG. 8 is a flow chart detailing the centrifugation process of the amniotic fluid.
Figure 9:
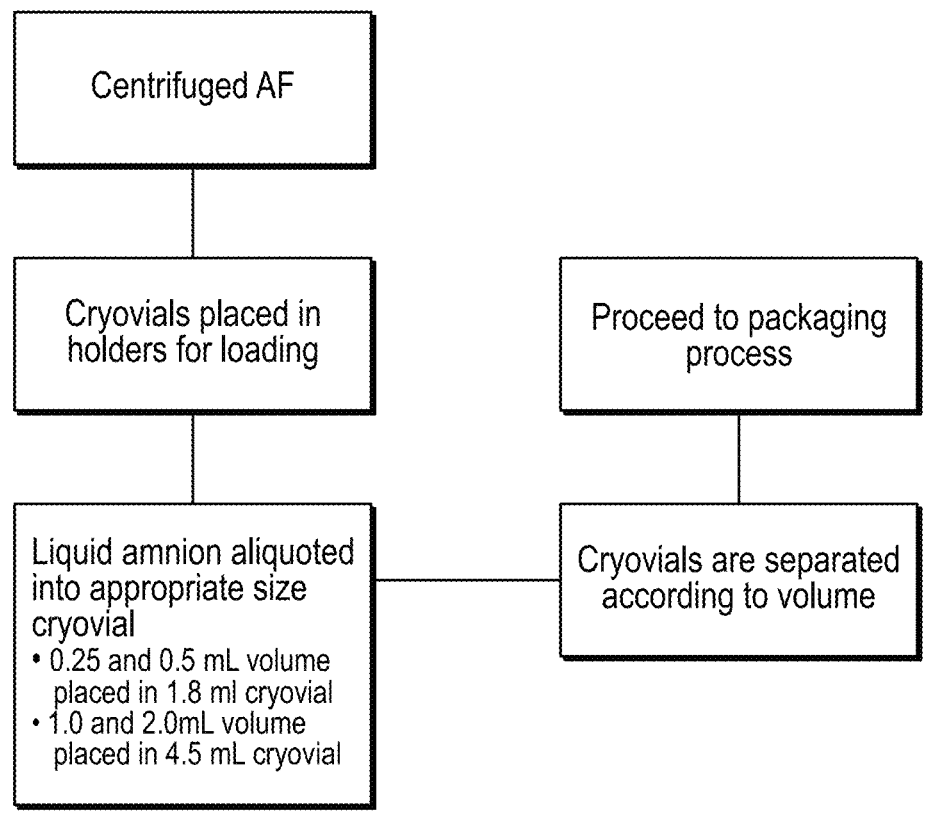
FIG. 9 is a flow chart detailing the aliquoting process of the amniotic fluid.

With reference to FIG. 4, the material once centrifuged, is separated wherein a supernatant 4 is formed along with a solid pellet of debris. The supernatant 4 is carefully pipetted out from the container 20 after centrifuging leaving the debris. An important aspect of the filtering shown in the photographs of FIGS. 1-3 is that the porosity of the blood filter 16 used is approximately 170 to 260 microns. This means that particles and cell fragments below 170 microns are clearly passed through the filter 16 to be centrifuged. Some as high as 260 microns can pass through the filter 16 depending on the filter pore size. In this range, it has been found that a large volume of the particularly beneficial cell fragments and cellular material can be passed into the filtered amniotic fluid. At this point the amniotic fluid 2 is moved into centrifuge tubes 20. The centrifuge tubes 20 receive a volume of material to be spun for a short duration at a relatively low or moderately low speed. Once the material is effectively spun for 5 minutes at 400 g, the pellet is formed in the bottom of the tube and the supernatant 4 can be pipetted off as discussed. Once this occurs, the supernatant 4 is carefully removed and the centrifugation process is finished as diagrammed in FIG. 8. Once the aliquoting process is completed and the supernatant 4 is divided into cryovials 40, it is recommended that 0.25 to 0.5 ml supernatant 4 material be placed in small vials 40 as shown in FIGS. 4-6. The small vials 40 are approximately 1.8 ml in volume. Larger volumes from 0.1 to 2.0 ml can be maintained in larger cryovials 40 of 4 ml or greater. These are then cryogenically frozen. FIG. 4 shows the supernatant 4 directly after centrifuge process wherein FIG. 5 shows the frozen supernatant 4 from the amniotic fluid 2 after the centrifuge process. FIG. 6 shows a clear supernatant 4 from the amniotic fluid 2 after the centrifuge process.

As shown, the frozen or liquid supernatant 4 taken from the filtered and centrifuged amniotic fluid 2 can have a very light pink to translucent color either in the frozen or the liquid form. This indicates that the material contains no immunological artifacts that could cause a problem when injected into a patient. As illustrated, the finished transplant product 100 will be non-immunogenic and maintain the biochemical properties found in the naturally occurring amniotic fluid. The advantage of the present invention is that a much larger array of particles and cell fragments and cellular material from the amniotic fluid will be passed through the blood filter and yet surprisingly, due to the processing technique this material will maintain its sterility and its non-immunogenic characteristics if properly handled using aseptic techniques described in the present invention. If however, the material is allowed to be collected and recovered wherein the fluid color is reddish or dark reddish, it is noted that this material would not be a proper source of amniotic fluid from which a transplantable product 100 can be manufactured.

Figure 10:
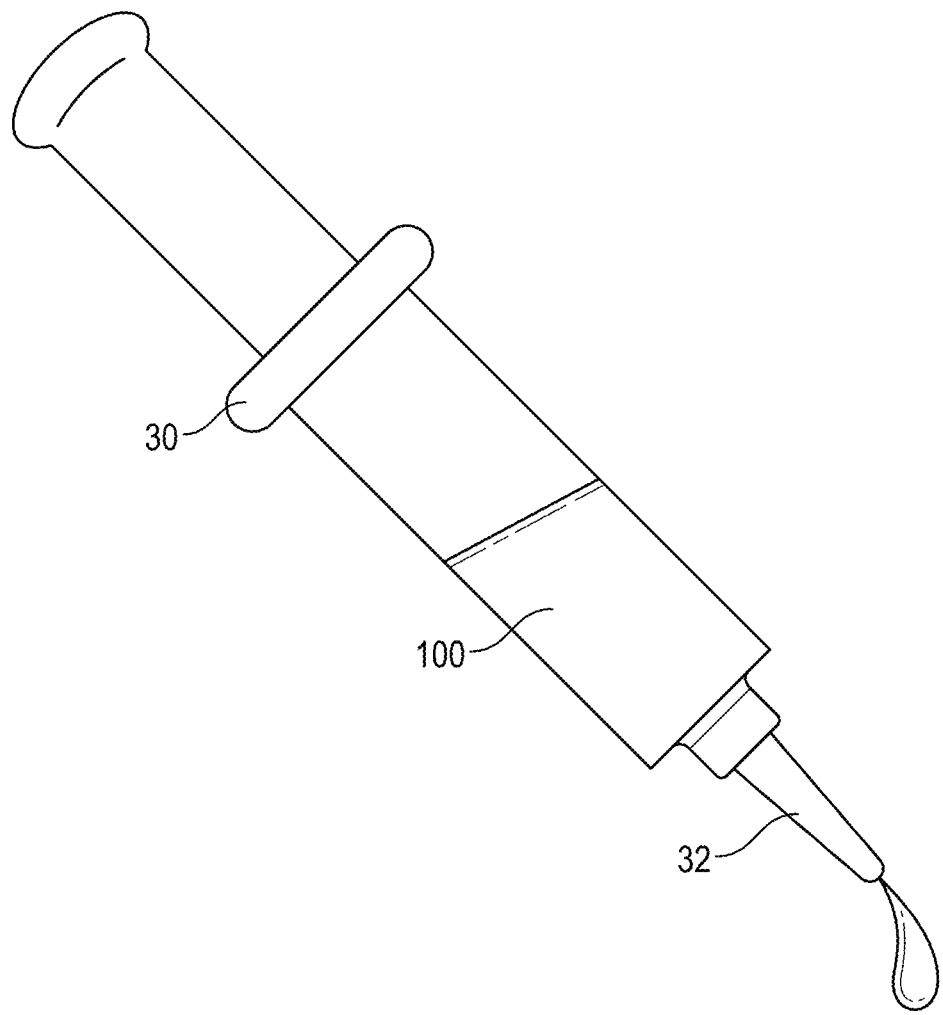
FIG. 10 is a perspective view of a syringe with the transplant product.

The benefits of the above referenced transplant product 100 made from the supernatant of the filtered and centrifuged properly colored or clear amniotic fluid is that it can be used to treat a variety of conditions, in particular skin conditions or any soft tissue conditions wherein a regenerative outcome is anticipated or desired. In the case of degenerative material, it is possible that injecting the amniotic fluid in the region to be treated will have a beneficial outcome with regard to the condition. Under these circumstances, it has been determined that the transplantable material ideally should be suitable for injection directly into a patient when resuspended in a diluent after thawing. To have this occur, the filtration was set such that the particle size would not occlude or block a small gauge needle such as a 30 gauge needle 32. Accordingly, in preparing the supernatant 4, from its thawed unfrozen stated it is recommended that it be diluted with sterile water or other suitable diluent to form the liquid amnion transplant product 100 which is then drawn through a syringe 30 as shown in FIG. 10, for later injection into the patient. Preferably, this is done on site and at the time of the injection. Once this is accomplished, the transplant product 100 collected in the syringe 30 can be injected directly into the patient into the area to be treated or can be provided as a topical spray through a spray nozzle attached to the syringe or other dispensing device.

The advantage of the present invention as compared to the prior art is that the centrifugation only occurs in 5 minutes is accomplished at a low rpm of 400 g and this removes the unwanted and undesirable debris particles and blood cells from the amniotic fluid. As a result, the material is left in a rather pristine state, unaltered biochemically by the processing techniques. The prior art recommended filtration down to 0.2 microns which will eliminate any microbiological remnants from the fluid, however, in doing so a tremendously large volume of the beneficial biochemical properties of the amniotic fluid is screened and filtered from the resultant supernatant. Furthermore, the spinning of the supernatant at 10 times the gravity recommended in the present invention, means that a larger debris button is created. The end product is an amniotic fluid that basically approaches the value of sterile water. This leaves very little of the constituent biologic value for the product. In the prior art mentioned in the background of this invention, it is noted that the supernatant made from the amniotic fluid was used as an eye droplet and therefore very minor improvements in the biochemical properties compared to water may be beneficial for the treatment of an eye as the larger particles in the present product 100 could be adverse to surface treating an eye. In most other areas where a more meaningful and more aggressive treatment is expected, it is believed that the present invention provides orders of magnitude superior biochemical properties including growth factors that will help in the regeneration of tissue.

Developmental research testing has confirmed the existence of preserved growth factors including TIMP-2, HGF, TIMP-3, TIMP-1, IGF-2, IL-6, IGF-1, GRO-alpha, TGF-B2, TGF-B1, IL-1RA, TIMP-4, MCP-1, EGF, TGF-alpha and TNF-alpha that aid in wound healing.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A liquid amnion transplant product comprising a supernatant from filtered and centrifuged amniotic fluid:
   wherein the amniotic fluid when recovered aseptically has a clear, translucent to slightly pink or tan color; wherein the supernatant having been taken from the amniotic fluid which had passed through a 170-260 micron blood filter; wherein the filtered amniotic fluid then having been centrifuged and the supernatant is further separated from a pellet of debris particles of a size as high as 260 microns, leaving the supernatant containing cellular material or cell fragments set at a particle size so the isolated supernatant does not block a 30 gauge needle (152 microns) and retains biochemical properties.

2. The liquid amnion transplant product of claim 1, wherein the product is cryofrozen in a volume of 0.25 to 2.0 ml in a cryovial.

3. A method for producing a transplant product, comprising the steps of:
   a) obtaining a volume of greater than 100 ml of sterile human amniotic fluid from a woman, wherein the volume has a pink to clear color and contains no vernix;
   b) filtering the amniotic fluid through a blood filter with a pore size of 170 to 260 microns;
   c) and centrifuging the filtered amniotic fluid to produce a pellet of debris particles of a size as high as 260 microns and a supernatant that is the transplant product, wherein the supernatant contains cellular material or cell fragments of a particle size less than 260 microns, wherein the supernatant does not block a 30 gauge needle (152 microns), and wherein the supernatant has the biochemical properties of the tissue intact.

* * * * *